(12) United States Patent
Shimada et al.

(10) Patent No.: US 8,764,636 B2
(45) Date of Patent: Jul. 1, 2014

(54) ELECTRONIC ENDOSCOPIC APPARATUS

(75) Inventors: Atsushi Shimada, Tokyo (JP); Yusuke Yabe, Tokyo (JP); Tomoya Takahashi, Tokyo (JP); Susumu Hashimoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1569 days.

(21) Appl. No.: 11/916,918

(22) PCT Filed: Apr. 27, 2006

(86) PCT No.: PCT/JP2006/308882
§ 371 (c)(1),
(2), (4) Date: Dec. 7, 2007

(87) PCT Pub. No.: WO2006/137220
PCT Pub. Date: Dec. 28, 2006

(65) Prior Publication Data
US 2009/0227839 A1 Sep. 10, 2009

(30) Foreign Application Priority Data
Jun. 21, 2005 (JP) ................................. 2005-181153
Jul. 4, 2005 (JP) ................................. 2005-195407

(51) Int. Cl.
*A61B 1/00* (2006.01)
*A61B 1/04* (2006.01)

(52) U.S. Cl.
USPC ........................................................ 600/118

(58) Field of Classification Search
USPC ............. 348/76, 176, 178; 600/118, 103, 117
See application file for complete search history.

(56) References Cited

U.S. PATENT DOCUMENTS

| 5,408,263 | A | 4/1995 | Kikuchi et al. | |
| 5,868,666 | A | 2/1999 | Okada et al. | |
| 5,892,961 | A * | 4/1999 | Trimberger ..................... | 712/10 |
| 6,638,212 | B1 | 10/2003 | Oshima | |
| 2003/0025789 | A1* | 2/2003 | Saito et al. ...................... | 348/76 |
| 2004/0263643 | A1 | 12/2004 | Imaizumi et al. | |

FOREIGN PATENT DOCUMENTS

| CN | 2519335 Y | 10/2002 |
| CN | 1510565 A | 7/2004 |
| CN | 1578471 A | 2/2005 |

(Continued)

OTHER PUBLICATIONS

Extended European Search Report dated Jan. 25, 2011.

(Continued)

*Primary Examiner* — Anhtuan T Nguyen
*Assistant Examiner* — Rynae Boler
(74) *Attorney, Agent, or Firm* — Scully, Scott, Murphy & Presser, P.C.

(57) ABSTRACT

An electronic endoscopic apparatus of the present invention can improve the usage efficiency of a circuit of a control section therein and can improve the reliability of operations of the circuit. The electronic endoscopic apparatus is an electronic endoscopic apparatus having multiple operation modes to be executed exclusively, the apparatus internally including an FPGA 1 that internally includes a CPU 10 and peripheral circuits and controls the execution of the operation modes and a switching request detecting section that detects a request for switching to the operation mode to be executed, wherein the internal configuration of the FPGA 1 is changed based on the detection result by the switching request detecting section.

5 Claims, 9 Drawing Sheets

(56) References Cited

FOREIGN PATENT DOCUMENTS

| | | |
|---|---|---|
| EP | 1 177 761 A2 | 2/2002 |
| JP | 05-019019 | 1/1993 |
| JP | 6-37777 | 2/1994 |
| JP | 06-090900 | 4/1994 |
| JP | 10-028671 | 2/1998 |
| JP | 2002-045330 | 2/2002 |
| JP | 2003-122600 | 4/2003 |
| JP | 2003-167738 | 6/2003 |
| JP | 2003-339635 | 12/2003 |
| JP | 2005-013611 | 1/2005 |
| JP | 2005-103325 | 4/2005 |
| JP | 2005-131363 | 5/2005 |
| JP | 2005-342147 | 12/2005 |

OTHER PUBLICATIONS

Extended Supplementary European Search Report dated Apr. 23, 2010.

* cited by examiner

ELECTRONIC ENDOSCOPIC APPARATUS

TECHNICAL FIELD

The present invention relates to an electronic endoscopic apparatus.

BACKGROUND ART

In recent years, an endoscopic apparatus that can perform a treatment by observing an organ in a body cavity and/or by using a treatment instrument through a treatment instrument channel as required has been widely used as medical equipment. In industrial fields also, an industrial endoscope has been widely used for observing/examining a flaw or corrosion, for example, within a small-diameter tube of a boiler, a turbine, an engine, a chemical plant and so on.

An endoscopic apparatus mainly includes a light source device that irradiates illumination light, an insertion section to be inserted into a body cavity or a small-diameter tube, and an operation section that operates to bend the insertion section. Illumination light transmitting means and/or observation light transmitting means are provided in the part from the operation section to the insertion section. The illumination light transmitting means may be a light guide fiber bundle that transmits illumination light to the end of the insertion section. The observation light transmitting means may be an image guide that transmits light from a subject obtained by irradiating illumination light thereto. The operation section includes an eye piece section for observing, by unaided eyes, the light from a subject transmitted through the image guide, for example, and a connecting section to the light source device for inputting predetermined illumination light to the light guide, for example.

As disclosed in Japanese Unexamined Patent Application Publication No. 2005-103325, an electronic endoscopic apparatus has been developed and practically used that can display an electronic image of an observed part on a monitor, for example, by providing a solid-state image pickup device such as a CCD at the end of the insertion section or the image guide end of the operation section, forming an image from the light from the observed part due to the illumination light outputted from the light guide onto an image pickup surface by an objective optical system, converting the light to an electric signal, and performing signal processing on the electric signal.

Even in a case where an electronic endoscopic apparatus used as a medical machine has a failure or an abnormality during a medical treatment, obtaining and operating a minimum function for performing the medical treatment is required. For this reason, an electronic endoscopic apparatus has operation modes for operations for different processing details, such as an operation for performing a normal medical treatment and an operation for a case where a failure occurs within the apparatus. The operation mode can be switched in accordance with an external mode instruction or the state of the apparatus. Notably, providing multiple operation modes allows each operation mode to check the other operation modes. Thus, whether the operation mode to be switched will operate normally or not can be checked before the operation mode is switched, which can advantageously improve the safety level.

Figure 6:
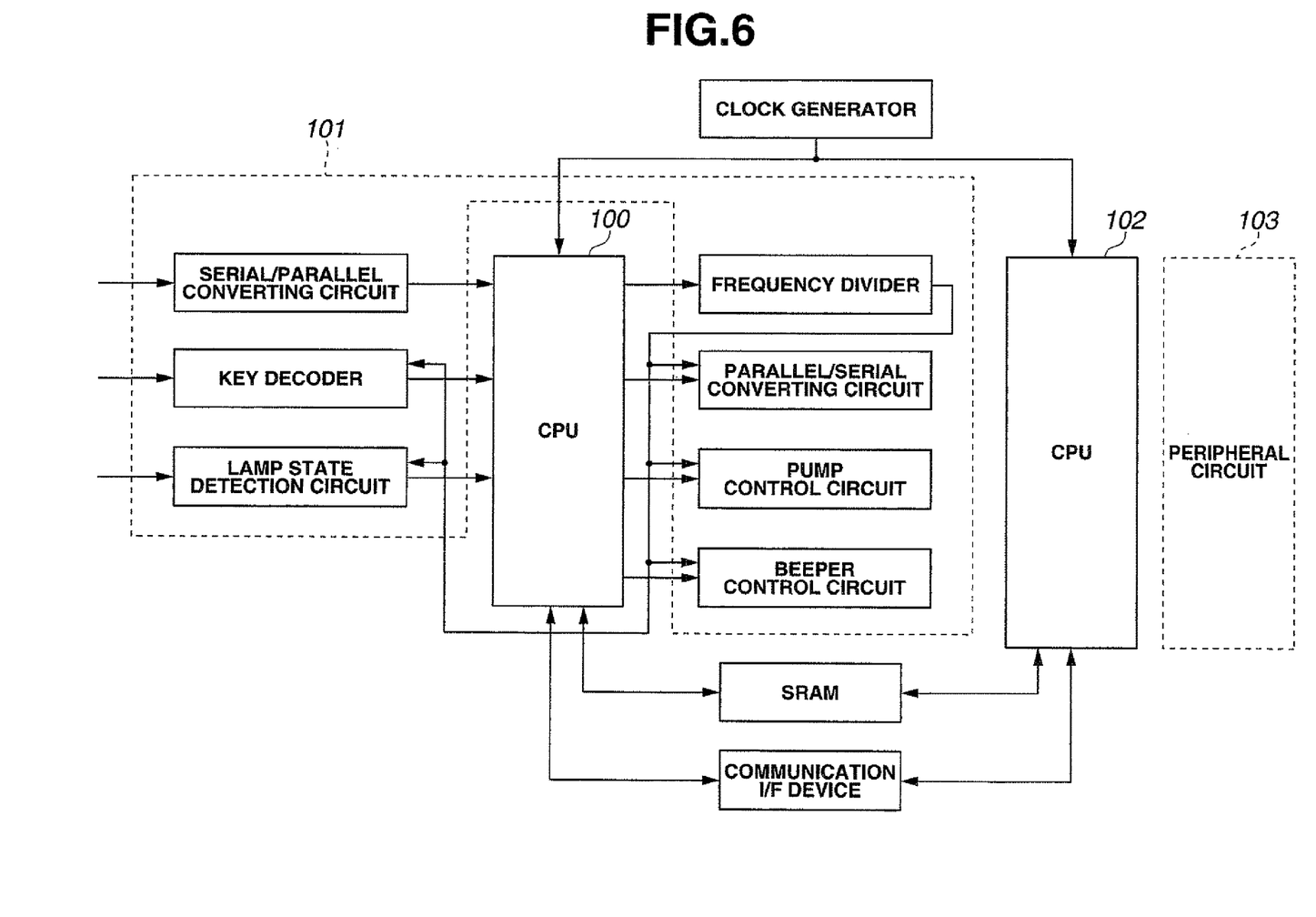
FIG. 6 is a block diagram illustrating a configuration of a control section of a conventional electronic endoscopic apparatus.

The control section of an electronic endoscopic apparatus includes circuits for controlling components of the apparatus in accordance with the set values, which are inputted in advance, or an external operation instruction. Since the circuit to be used differs according to the operation mode, the circuit to be used is switched when the operation mode is switched. In a conventional electronic endoscopic apparatus, as shown in FIG. 6, a CPU and a peripheral circuit required for an operation are prepared and implemented for each operation mode. FIG. 6 is a block diagram illustrating the configuration of the control section of a conventional electronic endoscopic apparatus. For example, two operation modes may be defined including a normal use mode, which is an operation mode for performing a normal medical treatment, and a safety mode, which is an operation mode in a case where some failure occurs within the apparatus. In this case, as shown in FIG. 6, the control section includes a CPU 100 and peripheral circuit 101 for use in the normal mode and a CPU 102 and peripheral circuit 103 for use in the safety mode.

In a case where the operation modes are implemented on one substrate in the electronic endoscopic apparatus, the multiple CPUs 100 and 102 and the peripheral circuits 101 and 103 must be implemented on the substrate, which may disadvantageously increases the area of the substrate. In addition, since the multiple operation modes are not implemented simultaneously, the CPU 102 and peripheral circuit 103 are not used when the normal use mode is implemented while the CPU 100 and peripheral circuit 101 are not used when the safety mode is implemented. For this reason, the usage efficiency may be disadvantageously decreased.

In order to solve the problems, a method may be considered that can decrease the size of the circuits and improve the usage efficiency of the circuits by parenthesizing a circuit that can be used in common to commonly use the circuit as a common circuit in both operation modes or increase the implementation density of the circuit. However, in a case where the circuit to be used in each operation mode and the common circuit are placed at remote positions from each other or the circuit to be used in the other operation mode must be separated, the signal path may be complicated. Then, even though the common circuit can be theoretically parenthesized, the implementation may be physically difficult, which is a problem. In addition, since a high implementation density of the circuit may not allow a sufficient clearance between signal lines or between circuits, the possibility increases that a short circuit may be established or an improper operation may occur due to the contact between the signal lines or parts, which may disadvantageously decrease the reliability.

Such an electronic endoscopic apparatus includes a controller for controlling components of the apparatus in accordance with set values, which are inputted in advance, or an external operation instruction. In a case where the controller includes a CPU (central processing unit), an FPGA (Field Programmable Gate Array) and a CPLD (Complex Programmable Logic Device), abnormality monitoring means is generally provided therein that includes runaway detection means for detecting their runaway and reset means for resetting the controller and initializing an operation if the state that the controller runs away is detected in order to prevent causing damage on the controlled machine from the operation of the runaway controller.

A watch dog timer is widely known and is generally used as the abnormality monitoring means. The watch dog timer is directly connected to a controller to be monitored and monitors pulse signals at predetermined intervals for clearing the timer implemented in software by the controller by controlling the output port in order to monitor whether the controller is operating normally or not. The watch dog timer then outputs a reset signal to the controller in a case where the controller has an abnormal operation state and cannot output a pulse signal and no pulse signals occur in a certain period of time. During the timeout period from the time when the timer is cleared to the time when the reset is outputted, each watch dog timer has an inherent value, and a watch dog timer suitable for the specifications of the controller must therefore be selected to use.

However, in a case where the controller of an electronic endoscope includes an FPGA and a CPLD, which internally includes a CPU, the initialization of software is not started until the configuration completes upon power-up of the apparatus. For this reason, it takes time to start up the CPU. In a case where a watch dog timer is selected that has a shorter time out period than the startup time of the CPU, the pulse signals at predetermined cycles for clearing the timer are not outputted during the startup of the CPU. Then, the reset is outputted during the startup of the CPU, and the apparatus may be repetitively restarted upon power-up.

In order to avoid the problem, a watch dog timer having a longer timeout period than the startup time of the CPU must be used. In this case, the repetitive restart can be prevented upon power up of the CPU, but the timing for starting the reset may be delayed in a case where the CPU runs away during diagnosis or observation. For example, in a case where the CPU runs away when the insertion section is in a body cavity, the apparatus may perform an improper operation that possibly hurts the body cavity. Therefore, there is a problem that it is difficult to use a watch dog timer having a longer timeout period for safety problem in a medical apparatus such as an electronic endoscope.

Accordingly, it is an object of the present invention to provide an electronic endoscopic apparatus that can improve the usage efficiency of the circuit of a control section and improve the reliability of operations of the circuit.

It is another object of the present invention to provide an electronic endoscopic apparatus that can prevent a CPU from repetitively restarting even when a watch dog timer having a shorter timeout period than the startup time of the CPU.

DISCLOSURE OF INVENTION

Means for Solving the Problem

An electronic endoscopic apparatus according to a first aspect of the present invention is an electronic endoscopic apparatus having multiple operation modes to be executed exclusively, the apparatus including a control section that controls the execution of the operation modes, and a switching request detecting section that detects a request for switching to the operation mode to be executed, wherein the internal configuration of the control section is changed based on the detection result by the switching request detecting section.

An electronic endoscopic apparatus according to a second aspect of the present invention includes a controller that outputs a first pulse signal during a normal operation, a dummy pulse generating section that generates a second pulse signal, a completion-of-startup detecting section that detects the completion of the startup of the controller, an abnormality monitoring signal generating section that outputs one of the first pulse signal and the second pulse signal as an abnormality monitoring signal based on the detection result of the completion-of-startup detecting section, and an abnormality detecting section that detects an abnormality in the controller based on the abnormality monitoring signal and outputs a reset signal.

BRIEF DESCRIPTION OF THE DRAWINGS

FIGS. 4A and 4B are block diagrams illustrating an internal configuration of an FPGA relating to communication with an external machine.

BEST MODE FOR CARRYING OUT THE INVENTION

With reference to drawings, embodiments of the present invention will be described below.

[First Embodiment]

A first embodiment will be described based on a case where four operation modes, which will be described later, are defined in an electronic endoscopic apparatus. An electronic endoscopic apparatus according to the present embodiment is an apparatus the internal circuit configuration of which can be changed in accordance with the operation mode.

A first operation mode is a normal use mode, which is an operation mode for a case where the electronic endoscopic apparatus is normally used. The normal use mode implements functions of control over a front panel, not shown, on the electronic endoscopic apparatus for inputting an operation instruction by a user, communication between the electronic endoscopic apparatus and a peripheral machine, lighting on/off and dimming of a lamp, not shown, on an electronic endoscopic apparatus, control of driving sections within a cabinet for operating components of the electronic endoscopic apparatus, control over air feeding pump and control over the output by an alarm when a temperature error due to an abnormal increase in temperature within the cabinet or an abnormality in various driving sections is detected by an internal error detecting section (output of a beeper sound or display of text on the front panel), for example.

A second operation mode is a writing mode, which is an operation mode for writing data to a non-volatile memory 2, which will be described later, The writing mode implements an operation of writing configuration data (configuration data on a circuit within an FPGA) or software to be executed by a CPU 10 within the FPGA 1 from an external writing apparatus to the non-volatile memory 2. A third operation mode is a factory shipment mode, which is an operation mode for performing internal setting or operation check when the electronic endoscopic apparatus is shipped from a factory.

A fourth operation mode is a safety mode, which is an operation mode for a case where the electronic endoscopic apparatus is failed. If a failure within the electronic endoscopic apparatus is detected, the safety mode implements functions of securing the lighting on of a lamp on an optical axis of illumination light irradiated from a light source device, not shown, securing an operation by the air feeding pump, and display of the error on the front panel, for example.

Figure 1:
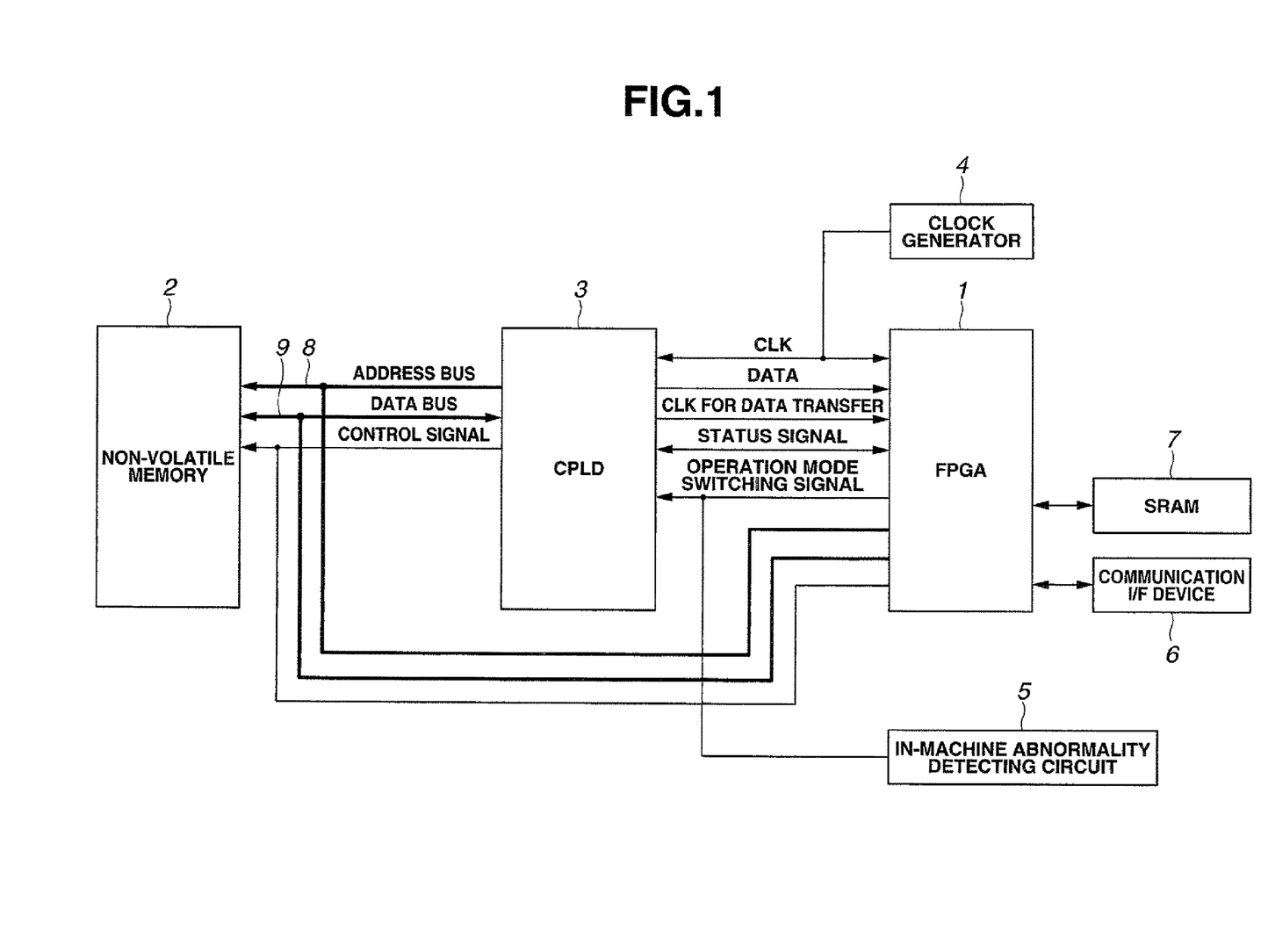
FIG. 1 is a block diagram illustrating a configuration of a control section of an electronic endoscopic apparatus according to a first embodiment of the present invention.

First of all, with reference to FIG. 1, a configuration of a control section of the electronic endoscopic apparatus according to an embodiment of the present invention will be described. FIG. 1 is a block diagram illustrating a configuration of a control section of an electronic endoscopic apparatus according to an embodiment of the present invention. Only a part relating to switching of operation modes in the control section will be described herein.

As shown in FIG. 1, the control section of an electronic endoscopic apparatus according to an embodiment of the present invention includes an FPGA (Field Programmable Gate Array) 1 internally having the CPU (central processing unit) 10, the non-volatile memory 2 storing software to be executed by the CPU 10 in the FPGA 1 and configuration data according to the operation mode, CPLD (Complex Programmable Logic Device) 3 having a circuit, not shown, for downloading data from the non-volatile memory 2 to the FPGA 1, a clock generator 4 that generates clock signals CLK and outputs them to the FPGA 1 and CPLD 3, an in-machine abnormality detecting circuit 5 that detects an internal abnormality of the electronic endoscopic apparatus, a communication I/F device 6 for communicating with an external apparatus and an SRAM 7.

The FPGA 1, non-volatile memory 2 and CPLD 3 are electrically connected with each other via an address bus 8 and a data bus 9. The non-volatile memory 2 stores, as shown in FIG. 2, configuration data of the FPGA 1 to be used by each operation mode and software to be executed by the CPU 10.

Figure 2:
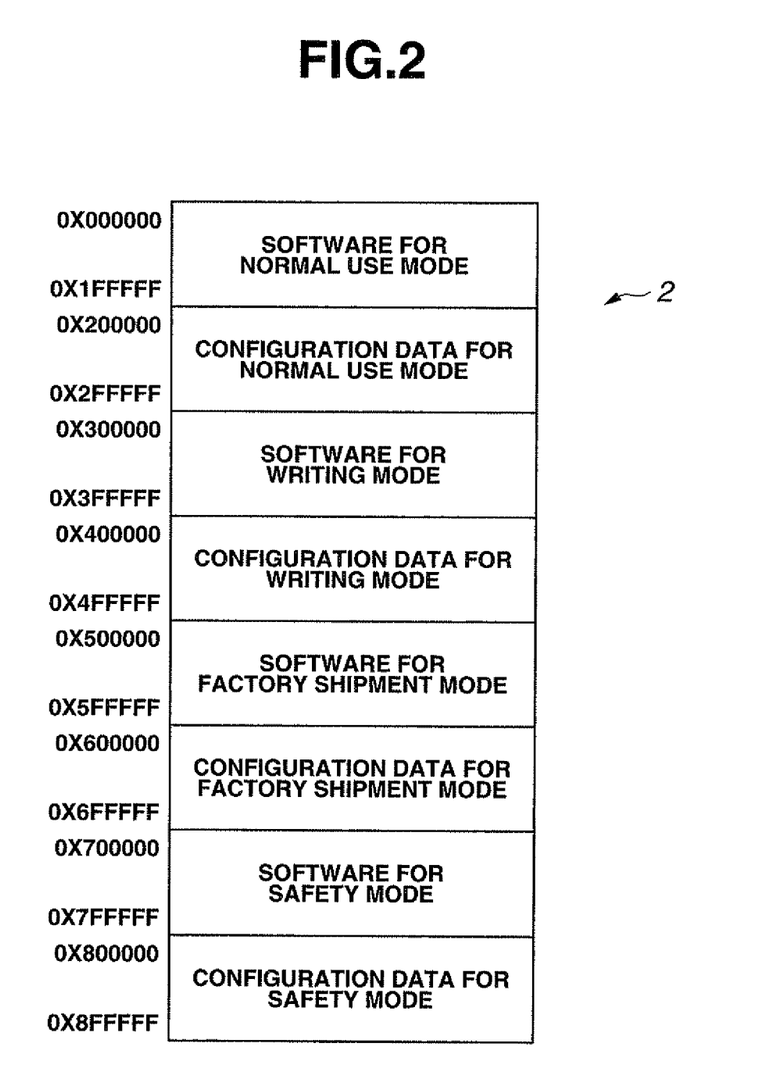
FIG. 2 is a diagram illustrating an internal configuration of a non-volatile memory.

FIG. 2 is a diagram illustrating an internal configuration of the non-volatile memory 2. For example, as shown in FIG. 2, the inside of the non-volatile memory 2 is divided into blocks The block of addresses 0x0000 to 0x1FFFFF stores software to be executed by the CPU 10 in the normal use mode. The block of addresses 0x200000 to 0x2FFFFF stores configuration data in the normal use mode. The block of addresses 0x300000 to 0x3FFFFF stores software to be executed by the CPU in the writing mode. The block of addresses 0x400000 to 0x4FFFFF stores configuration data in the writing mode. The block of addresses 0x500000 to 0x5FFFFF stores software to be executed by the CPU 10 in the factory shipment mode. The block of addresses 0x600000 to 0x6FFFFF stores configuration data in the safety mode. The block of addresses 0x700000 to 0x7FFFFF stores software to be executed by the CPU 10 in the safety mode. The block of addresses 0x800000 to 0x8FFFFF stores configuration data in the safety mode.

In this way, the software and configuration data for all of the operation modes are stored in one non-volatile memory 2, and the configuration data and software according to the operation mode to be executed are downloaded from the non-volatile memory 2 to the FPGA 1 to expand. More specifically, the address decoding is performed in a peripheral circuit of the CPU 10 in the FPGA 1 or the CPLD 3, for example, and a loading starting address corresponding to the operation mode to be executed is outputted to the non-volatile memory 2 via the address bus 8. In the non-volatile memory 2, the configuration data and software are extracted based on the inputted loading starting address and are downloaded to the FPGA 1 and/or CPLD 3 via the data bus 9.

Though the loading starting address can be selected when the software is designed, the memory management by software can be reduced by performing address decoding in a CPU peripheral circuit in the FPGA 1 or CPLD 3 and controlling, by hardware, the loading starting address corresponding to each operation mode. Notably, the address decoder is generally provided at the periphery of the CPU 10 but may be provided within the FPGA 1 in a case where the CPU 10 is provided within the FPGA 1 like the present embodiment.

A control signal, in addition to the loading starting address, is also outputted from the FPGA 1 and CPLD 3 to the non-volatile memory 2. A status signal is mutually communicated between the FPGA 1 and the CPLD 3. Data and/or a data transfer clock signal are further outputted from the CPLD 3 to the FPGA 1. An operation mode switching signal is further outputted from the FPGA 1 and in-machine abnormality detecting circuit S to the CPLD 3.

In the present configuration, the configuration data of the FPGA 1 and the software of the CPU 10 are downloaded by the CPLD 3 and non-volatile memory 2, but the CPLD 3 and non-volatile memory 2 may be implemented by one device (CPU or configuration device) satisfying those functions.

Next, the circuit configuration within the FPGA 1 will be described. The circuit configuration within the FPGA 1 is dynamically changed by the configuration data, which is downloaded from the non-volatile memory 2 and is internally expanded, and different circuit configurations are implemented for respective operation modes. However, since the CPU 10 is required in all of the operation modes, the circuit configurations having different peripheral circuits of the CPU 10 for respective operation modes are implemented.

Notably, since software downloaded from the non-volatile memory 2 is executed in the CPU 10, the function of the CPU 10 differs according to the operation mode. In other words, in the normal use mode, the CPU 10 performs control over operations on a front panel, not shown, and/or control over various operations involved in the communication with a peripheral machine. In the writing mode, the CPU 10 interfaces between the non-volatile memory 2 and an external machine. In the factory shipment mode, the CPU 10 interfaces with an external machine for writing an internal setting to the electronic endoscopic apparatus or checking operations. In the safety mode, the CPU 10 controls the lighting-on/off of the lamp or an air-feeding pump and/or a front panel, not shown.

Figure 3:
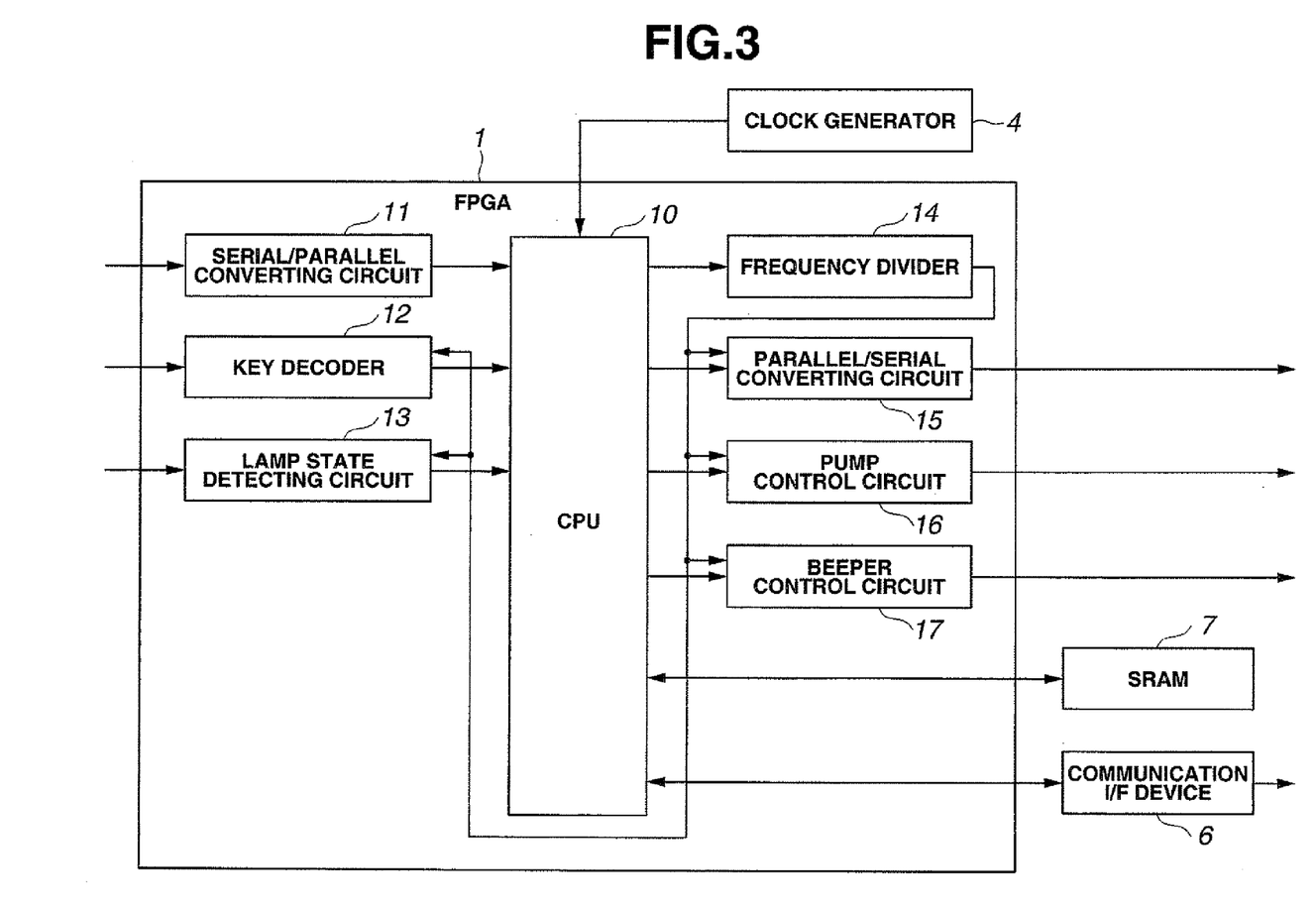
FIG. 3 is a block diagram illustrating a circuit configuration within an FPGA in a normal use mode.

With reference to FIG. 3, the circuit configuration within the FPGA 1 in the normal use mode will be described now. FIG. 3 is a block diagram illustrating the circuit configuration within the FPGA 1 in the normal use mode. In the normal use mode, the FPGA 1 internally includes the CPU 10 and includes peripheral circuits at the periphery of the CPU 10 including a serial/parallel converting circuit 11 for converting serial data transmitted from an external machine to parallel data, a key decoder 12, a lamp state detecting circuit 13 for detecting the state of a lamp provided on the electronic endoscopic apparatus, a frequency divider 14, a parallel/serial converting circuit 15 for converting the parallel data processed in the CPU 10 to the serial data and outputting the serial data, a pump control circuit 16 for controlling an air-feeding pump, and a beeper control circuit 17 that controls the output of a beeper sound when a temperature error due to an abnormal increase n temperature within the cabinet or an abnormality in various driving sections therein is detected by an internal error detecting section.

The usage efficiency of the circuits may be improved by configuring the CPU 10 and the peripheral circuit within the FPGA 1 in this way since only a required circuit can be constructed by dynamically changing the circuit within the FPGA 1 with the change in operation mode. Furthermore, since the required CPU and peripheral circuits for all of the operation modes are not necessarily implemented on the substrate, the size of the circuits and area of the substrate can be reduced, which can reduce the costs and can reduce the size of the apparatus.

Figure 4A:
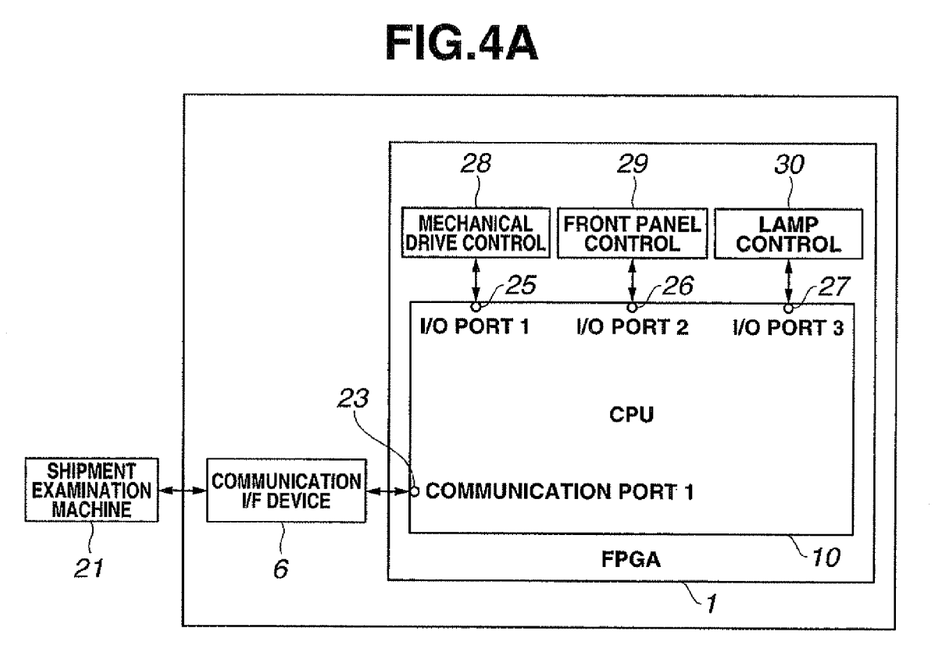
FIG. 4A is a block diagram illustrating an internal configuration of an FPGA in a factory shipment mode.
Figure 4B:
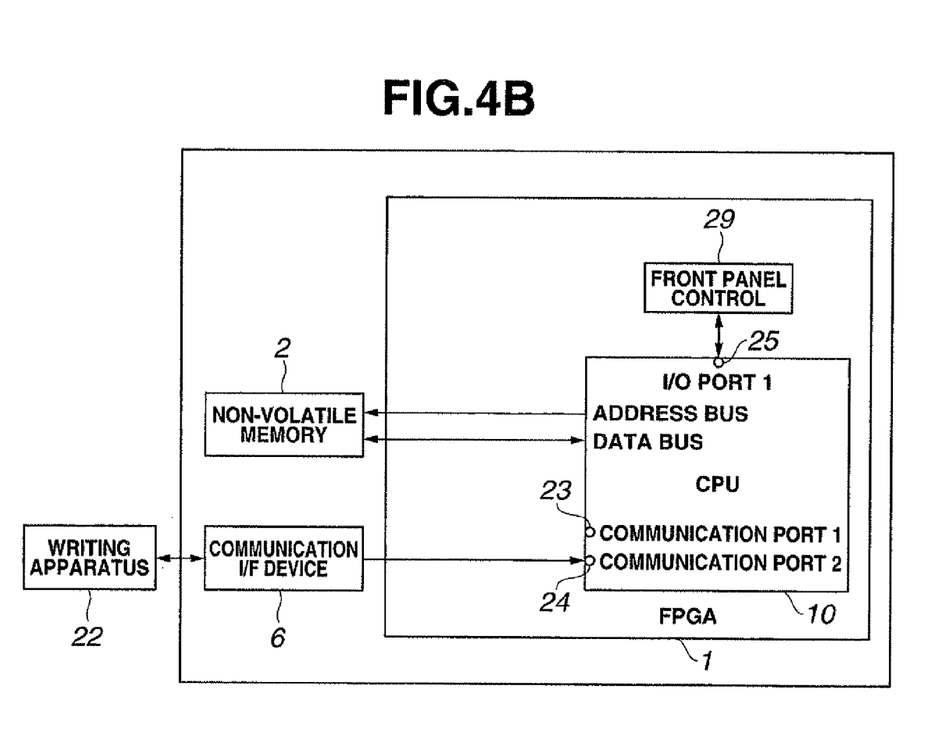
FIG. 4B is a block diagram illustrating an internal configuration of an FPGA 1 in a writing mode.

Next, the circuit change within the FPGA 1 in response to the switching of the operation modes will be described. Here, with reference to FIGS. 4A and 4B, the circuit change corresponding to the change from the factory shipment mode to the writing mode will be described by focusing on the circuit relating to communication with an external machine. FIGS. 4A and 4B are block diagrams illustrating the internal configurations of the FPGA 1 on communication with external machines. FIG. 4A is the internal configuration of the FPGA 1 in the factory shipment mode, and FIG. 4B is the internal configuration of the FPGA 1 in the writing mode.

As shown in FIG. 4A, the factory shipment mode requires a shipment examination communication line that allows communication between the CPU 10 and a shipment examination machine 21, which is an external machine, through the communication I/F device 6 such that the communication can be allowed between the shipment examination machine 21 and the electronic endoscopic apparatus for checking operations of the electronic endoscopic apparatus and/or performing internal settings such as a serial number thereof. As shown in FIG. 4B, the writing mode requires a writing communication line that allows communication between the CPU 10 and a writing apparatus 22, which is an external machine, through the communication I/F device 6 for obtaining configuration data of the FPGA 1 and software to be executed by the CPU 10 deployed within the FPGA 1 from the writing apparatus 22 and updating them to the non-volatile memory 2.

The factory shipment mode does not require the writing communication line, and the writing mode does not require the shipment examination communication line. In other words, both of the operation modes use one communication line only and do not use the shipment examination communication line and the writing communication line simultaneously. Therefore, the communication lines required by the operation modes can be provided by unifying the communication lines and switching the communication ports of the CPU 10, which are to be connected to the communication I/F device 6, according to the operation mode. Since the connection between the communication I/F device 6 and the terminal of the FPGA 1 is fixed by substrate wiring, the communication line can be changed with the change in operation mode by switching the connections between the terminal of the FPGA 1 and the CPU 10.

In other words, in the factory shipment mode, the shipment examination communication line can be provided by configuring the internal circuit of the FPGA 1 so as to connect the shipment examination machine 21 and the communication I/F device 6 and connect the terminal of the FPGA 1 connecting to the communication I/F device 6 and a first communication port 23 of the CPU 10. When the operation mode is switched from the factory shipment mode to the writing mode, the writing communication line is provided by changing the internal circuit of the FPGA 1 so as to connect the writing apparatus 22 and the communication I/F device 6 and connect the terminal of the FPGA 1 connecting to the communication I/F device 6 and a second communication port 24 of the CPU 10.

In this way, by changing the internal circuit of the FPGA 1 according to the operation mode, the first communication port 23 and second communication port 24 of the CPU 10 can communicate with an external machine connecting to the I/F device 6 according to the operation mode through the same communication I/F device 6. Thus, the separate allocation of the communication line required for each operation mode is not required in advance, and the communication line according to the operation mode can be configured on an ad hoc basis by changing the internal circuit of the FPGA 1.

Notably, in the factory shipment mode, the peripheral circuits of the CPU 10 within the FPGA 1 include a mechanical drive control circuit 28, a front panel control circuit 29 and a lamp control circuit 30, which are circuits for checking operations, in addition to the circuit relating to the communication with an external machine. The CPU 10 has first to third I/O ports 25 to 27 for connecting between the peripheral circuits and the CPU 10, which are to be connected to corresponding peripheral circuits. In the writing mode, a front panel control circuit 29 is provided within the FPGA 1 as a peripheral circuit of the CPU 10, in addition to the circuits relating to communication with an external machine. The front panel control circuit 29 is connected to the first I/O port 25, and the remaining second and third I/O ports 25 and 27 of the CPU 10 are not used. Further in the writing mode, the CPU 10 and the non-volatile memory 2 are connected via the address bus 8 and the data bus 9 since a loading starting address must be outputted to or data must be exchanged with the non-volatile memory 2.

Figure 5:
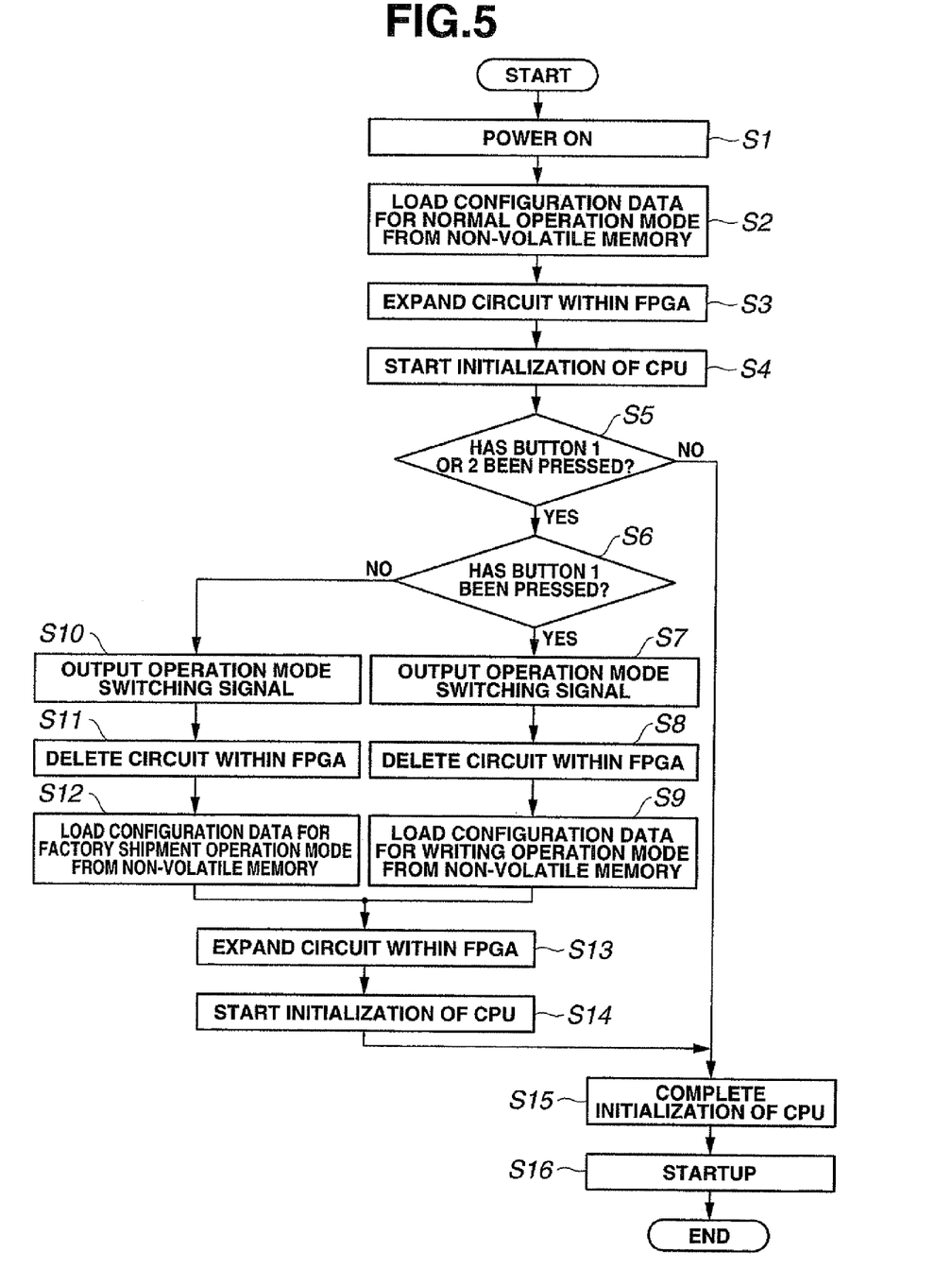
FIG. 5 is a flowchart describing steps of the startup of an electronic endoscopic apparatus.

Next, with reference to the flowchart in FIG. 5, the operation relating to the apparatus startup in the electronic endoscopic apparatus having the configuration as described above will be described. FIG. 5 is a flowchart describing steps of the startup of the electronic endoscopic apparatus. In a case where the electronic endoscopic apparatus is used for observation or treatment on a subject, the normal use mode is only selected. The possibility of causing a problem is high if the operation mode is easily switched, during observation or treatment on a subject, to the factory shipment mode or writing mode to be used for shipment examination or maintenance. For this reason, steps of the apparatus startup according to the present embodiment will be described by assuming that the normal use mode is selected by default and that the operation mode is switched only if an operation mode is intentionally selected.

As shown in FIG. 5, after the electronic endoscopic apparatus is powered on in step S1 first, the configuration data for the normal use mode is downloaded from the non-volatile memory 2 to the FPGA 1 via the data bus 9 in the subsequent step S2. Next, in step S3, based on the downloaded configuration data, the circuit for the normal use mode is expanded within the FPGA 1. The front panel, not shown, has buttons 1 and 2 for instructing to switch the operation mode by a user, and the expanded circuit includes a module that detects an operation on the buttons.

Subsequently, in step S4, the initialization of the CPU 10 is started. During the initialization of the CPU 10, a detecting circuit functioning as the switching request detecting section, which is included in the peripheral circuits of the CPU 10 always monitors whether the button 1 or 2 on the front panel has been pressed or not (step S5). If it is determined in step S5 that the button 1 or 2 on the front panel has not been pressed during the initialization of the CPU 10, the processing moves to step S15 where the initialization of the CPU 10 is completed. Notably, the buttons 1 and 2 are defined such that they can be enabled only if pressed during the initialization of the CPU 10 but can be disabled if pressed after the completion of the initialization in step S15. Upon completion of the startup of the apparatus once for the normal use mode, the operation mode can not be switched to the writing mode or factory shipment mode.

If it is determined in step 5 that the button 1 or button 2 on the front panel has been pressed during the initialization of the CPU 10, the processing moves to step S6 where the pressed button between the buttons 1 and 2 is determined.

If it is determined in step S6 that the pressed button is the button 1, the processing moves to step S7 where an operation mode switching signal for changing the operation mode to the writing mode is outputted from the FPGA 1 to the CPLD 3. In step S8, the CPLD 3 deletes the circuit within the FPGA 1 and outputs the loading starting address corresponding to the writing mode to the non-volatile memory 2 via the address bus 8. Subsequently, in step S9, the non-volatile memory 2 downloads the configuration data for the writing mode to the FPGA 1 via the data bus 9 in accordance with the received loading starting address, and the processing moves to step S13.

On the other hand, if it is determined in step S6 that the pressed button is the button 2, the processing moves to step S10 where an operation mode switching signal for changing the operation mode to the factory shipment mode is outputted from the FPGA 1 to the CPLD 3. The CPLD 3 in the subsequent step S11 deletes the circuit within the FPGA 1 and outputs the loading starting address corresponding to the factory shipment mode to the non-volatile memory 2 via the address bus 8. Subsequently, in step S12, the non-volatile memory 2 downloads the configuration data for the factory shipment mode to the FPGA 1 via the data bus 9 in accordance with the received loading starting address, and the processing moves to step S13.

In step S13, the circuit for the writing mode or factory shipment mode is expanded within the FPGA 1 based on the downloaded configuration data. Subsequently, the initialization of the CPU 10 is started in step S14, and the startup of the initialization of the CPU 10 is completed in step S15. Finally, in step S16, the startup of the selected operation mode is completed.

As described above, during the period from the powering-on to the completion of the initialization of the CPU 10, the apparatus is started up in the normal use mode if the buttons 1 and 2 are not pressed. If the button 1 is pressed, the apparatus is started up in the writing mode. If the button 2 is pressed, the apparatus is started up in the factory shipment mode. Having described the example in which the operation mode is switched based on the pressed button on the front panel, the instruction to switch the operation mode may be inputted in other manners according to the applications, such as transmission of a command from an external machine, remote transmission of a command through communication with an external machine, instruction of a command based on a switch on the substrate and instruction from an internal error detecting section of the apparatus. Alternatively, the operation mode may be switched by, in response to the receipt of an operation mode switching instruction, outputting the operation mode switching signal to a selected operation mode internally or externally from the FPGA 1 to the CPLD 3 and downloading and expanding the configuration data for the operation mode from the non-volatile memory 2 to the FPGA 1. Alternatively, the operation mode may be changed arbitrarily including after the completion of the startup.

In a case where the CPU 10 or a peripheral circuit within the FPGA 1 detects an in-machine abnormality such as an abnormality in internal temperature or in various driving sections during the operation of the apparatus in the normal use mode, an operation mode switching signal is outputted for switching the operation mode to the safety mode from the CPU 10 or a peripheral circuit within the FPGA 1 to the CPLD 3. The CPLD 3 deletes the circuit within the FPGA 1 and outputs the loading starting address corresponding to the safety mode to the non-volatile memory 2 via the address bus 8. The non-volatile memory 2 downloads the configuration data for the safety mode to the FPGA 1 via the data bus 9 in accordance with the received loading starting address. In the FPGA 1, the downloaded configuration data is expanded, and the switching of the operation mode from the normal use mode to the safety mode is completed.

In this way, in the electronic endoscopic apparatus of the present embodiment, the CPU 10 and peripheral circuits, which are required functions for operation modes, are provided within the FPGA 1, and the circuit inside of the FPGA 1 is dynamically changed with the change in operation mode. Thus, since the CPU and peripheral circuits required for all of the operation modes are not required to implement on the substrate, the size of the circuits to be implemented on the substrate and the substrate area can be reduced. Therefore, the usage efficiency of the circuits can be improved, and the costs can be reduced.

The configuration data may be downloaded from the non-volatile memory 2, and the circuit may be expanded within the FPGA 1 every time an operation mode is started without directly implementing the CPU 10 and the peripheral circuits on the substrate. Thus, the probability of occurrence of an implementation failure or circuit failure due to heat generation from the circuits, static electricity and deterioration over time can be reduced. Therefore, the quality, in particular, the reliability of the circuit operations can be improved.

Furthermore, in a case where maintenance is required against deterioration over time of the substrate, the circuit configurations used within the FPGA 1 and CPLD 3 are saved in the configuration data stored in the non-volatile memory 2. Thus, the circuit configurations can be diverted to other FPGA 1 and/or CPLD 3, and the necessity for considering alternatives of each part of the CPU 10 and the peripheral circuits may be eliminated. Therefore, the time and costs for the alternative consideration can be reduced.

As described above, according to the present embodiment, an electronic endoscopic apparatus can be provided that can improve the usage efficiency of the circuit of the control section and improve the reliability of the operations of the circuits.

[Second Embodiment]

Figure 7:
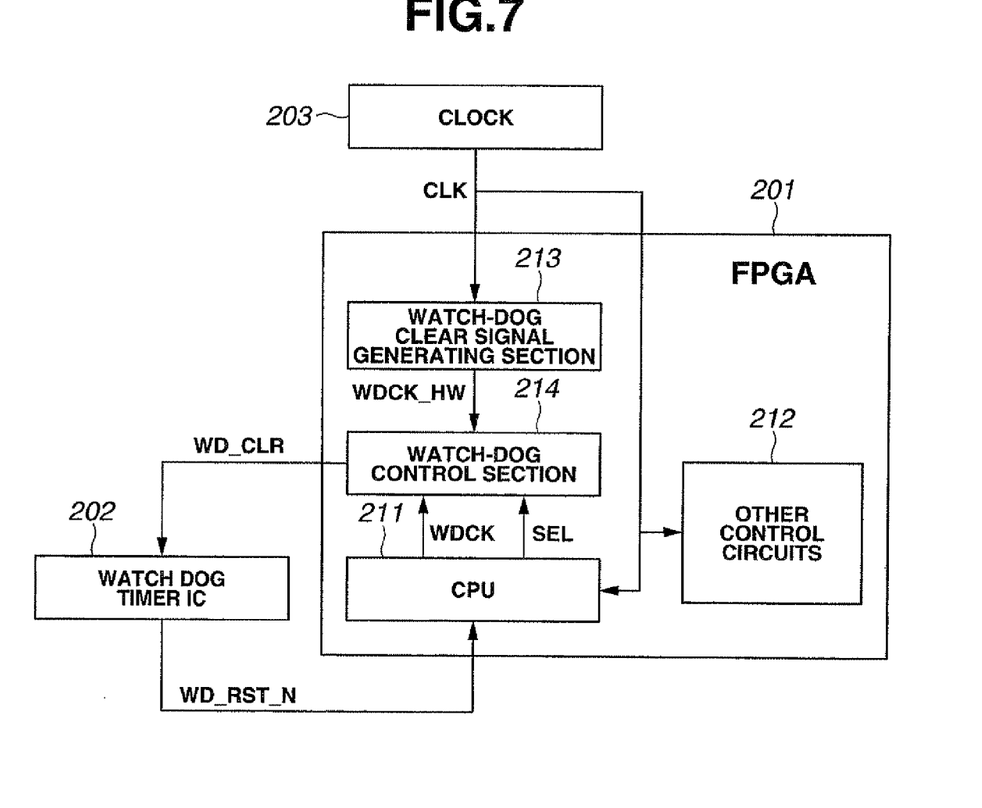
FIG. 7 is a block diagram illustrating a configuration of an abnormality monitoring section relating to a controller of an electronic endoscopic apparatus according to a second embodiment of the present invention.

First of all, with reference to FIG. 7, the entire configuration of an abnormality monitoring section relating to a controller of an electronic endoscopic apparatus according to a second embodiment of the present invention will be described. FIG. 7 is a block diagram illustrating the configuration of an abnormality monitoring section relating to a controller of an electronic endoscopic apparatus according to a second embodiment of the present invention.

As shown in FIG. 7, an abnormality monitoring section relating to a controller of an electronic endoscopic apparatus according to the second embodiment of the present invention includes an FPGA 201 that is a controller to be monitored, a watch dog timer IC 202 as an abnormality detecting section that detects an abnormality in the FPGA 201 and causes a reset operation and a clock 203 that generates a clock signal CLK and outputs the clock signal CLK to the FPGA 201.

The FPGA 201 includes a CPU 211, other control sections 212, a watch-dog clear signal generating section 213, and a watch-dog control section 214. The other control sections 212 control respective parts, such as a memory and a front panel, of the electronic endoscopic apparatus. The watch-dog clear signal generating section 213 functions as a dummy pulse generating section that generates a watch-dog-timer clear signal WDCK_HW based on a clock signal generated by the clock 203. The watch-dog control section 214 functions as a completion-of-startup detecting section and an abnormality monitoring signal generating section that control the watch dog timer IC 202. The clock signal CLK generated by the clock 203 is outputted to the CPU 211, other control sections 212 and watch-dog clear signal generating section 213. The FPGA 201 excluding a specific pin has a high impedance (Hi-Z) state, that is, is not electrically connected to other parts until the completion of the configuration.

The CPU 211 outputs a completion-of-initialization notification signal SEL indicating whether the initialization of software has been completed or not to the watch-dog control section 214. According to the present embodiment during the implementation of the initialization of software, LOW is outputted as the completion-of-initialization notification signal SEL. Upon completion of the initialization, HIGH is outputted as the completion-of-initialization notification signal SEL. A watch-dog-timer clear signal WDCK is also outputted from the CPU 211 to the watch-dog control section 214. The watch-dog-timer clear signal WDCK is a pulse signal at predetermined intervals but is not outputted during the implementation of the initialization of software and is outputted after the completion of the initialization, The watch-dog clear signal generating section 213 uses the clock signal CLK received from the clock 203 to generate a watch-dog clear timer signal WLDCK_HW at an arbitrary frequency, which is predefined by a designer, and output the signal to the watch-dog control section 214.

Based on the signal received from the CPU 211 and the watch-dog clear signal generating section 213, the watch-dog control section 214 generates a watch-dog timer-clear signal WD_CLR and outputs the signal to the watch dog timer IC 202. In other words, if the completion-of-initialization notification signal SEL received from the CPU 211 is LOW, the watch-dog clear timer signal WDCK_HW received from the watch-dog clear signal generating section 213 is outputted as the watch-dog-timer clear signal WD_CLR. If the completion-of-initialization notification signal SEL is HIGH, the watch-dog timer clear signal WDCK received from the CPU 211 is outputted as the watch-dog-timer clear signal WD_CLR.

However, the watch-dog control section 214 has a startup monitoring section that monitors the startup state of the controller. The watch-dog control section 214 further includes a counter, not shown, that counts the number of times of output of the watch-dog clear timer signal WDCK_HW received from the watch-dog clear signal generating section 213 as the watch-dog-timer clear signal WD_CLR (that is, the number of pulses). The startup monitoring section monitors whether the count value K of the counter has reached a predefined maximum number N of the number of pulses or not. If so, the watch-dog-timer clear signal WD_CLR is configured not to be outputted. This configuration can stop the output of the watch-dog-timer clear signal WD_CLR to the watch dog timer IC 202 if an abnormality occurs and the initialization is not completed during the startup of the CPU 211 and causes the watch dog timer IC 202 to output a reset signal WD_RST_N to the CPU 211, which can stop the runaway of the CPU 211.

If the watch dog timer IC 202 does not receive the input of the watch-dog-timer clear signal WD_CLR from the watch-dog control section 214 within a predetermined period after clearing the timer, the watch dog timer IC 202 generates a reset signal WD_RST_N and outputs the signal to the CPU 211. The predetermined period from the clearing of the timer to the output of the reset signal WD_RST_N is called timeout period and has a value predetermined by the watch dog timer IC 202.

Notably, the watch-dog-timer clear signal WD_CLR is not inputted from the watch-dog control section 214 to the watch dog timer IC 202 during the implementation of the configuration by the FPGA 201. Therefore, if the time for implementing the configuration by the FPGA 201 is longer than the timeout period, the reset signal WD_RST_N is outputted from the watch dog timer IC 202, which may possibly cause the reset. However, according to the present embodiment, the CPU 211 is configured within the FPGA 201, and the FPGA 201 excluding a specific pin has the high-impedance state. Therefore, the reset can be avoided even if the time for implementing the configuration by the FPGA 201 is longer than the timeout period.

Figure 8:
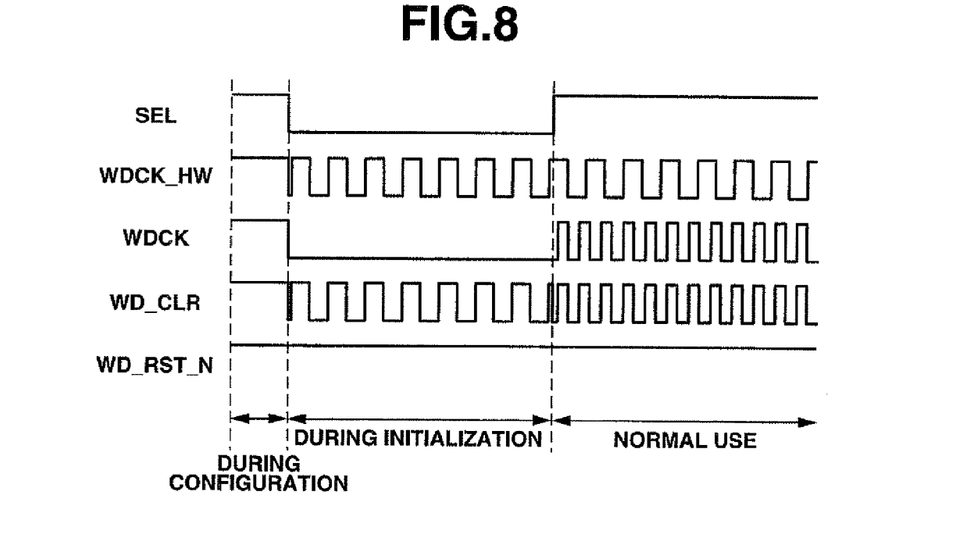
FIG. 8 is a timing chart illustrating an abnormality monitoring operation in a case where a CPU normally operates.
Figure 9:
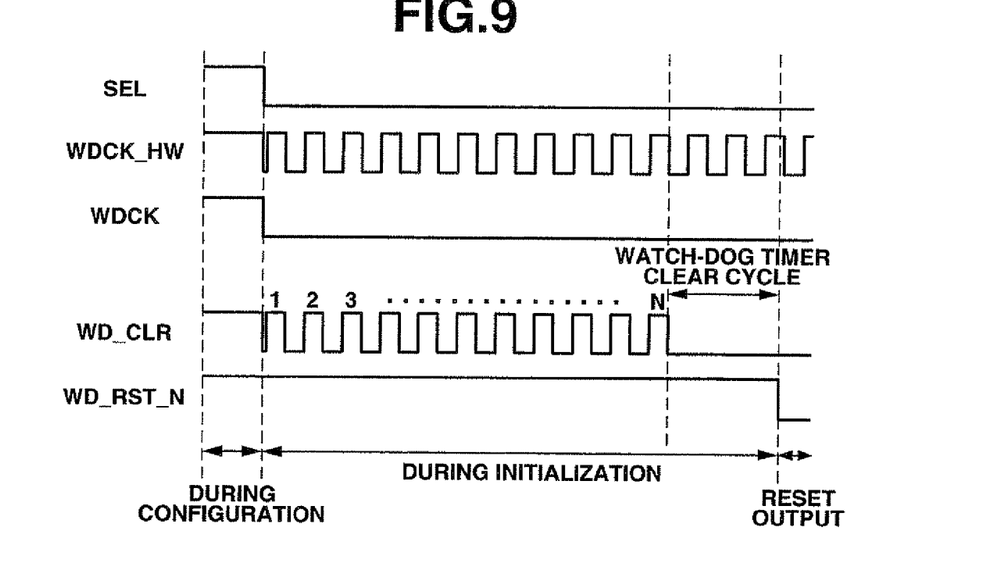
FIG. 9 is a timing chart illustrating an abnormality monitoring operation in a case where a CPU has an abnormality during the startup.

Next, with reference to the timing charts in FIGS. 8 and 9, an abnormality monitoring operation by the electronic endoscopic apparatus having the configuration above will be described. FIG. 8 is a timing chart illustrating an abnormality monitoring operation in a case where the CPU 211 is started normally. FIG. 9 is a timing chart illustrating an abnormality monitoring operation in a case where an abnormality occurs during the startup of the CPU 211.

First of all, with reference to the timing chart in FIG. 8, an abnormality monitoring operation in a case where the CPU 211 is started up normally will be described. First, upon powering on of the electronic endoscopic apparatus, the FPGA 201 implements the configuration. During the implementation of the configuration, a watch-dog-timer clear signal WD_CLR is not inputted from the watch-dog control section 214 to the watch dog timer IC 202. However, since, as described above, the FPGA 201 excluding a specific pin has the high impedance state, the reset signal WD_RST_N is not inputted to the CPU 211 configured within the FPGA 201 even if the time for implementing the configuration by the FPGA 201 is longer than the timeout period.

Upon completion of the configuration of the FPGA 201, the initialization of the CPU 211 is implemented. Thus, the completion-of-initialization notification signal SEL at LOW is outputted from the CPU 211 to the watch-dog control section 214. The watch-dog clear signal generating section 213 generates the watch-dog clear timer signal WDCK_HW, which is a pulse signal at arbitrary intervals, based on the clock signal CLK received from the clock 203 and outputs the signal to the watch-dog control section 214.

The watch-dog control section 214 outputs the watch-dog clear timer signal WDCK_HW received from the watch-dog clear signal generating section 213 to the watch dog timer IC 202 as the watch-dog-timer clear signal WD_CLR. In the watch-dog control section 214, the number of times of output of the watch-dog clear timer signal WDCK_HW as the watch-dog-timer clear signal WD_CLR (the number of outputted pulses) is counted by the counter, not shown.

The maximum value of the number of pulses of the watch-dog clear timer signal WDCK_HW, which is outputted to the watch dog timer IC 202 as the watch-dog clear timer signal WD_CLR during the period until the CPU 211 completes the initialization normally, is calculated based on design information and is defined as a maximum value N in the watch-dog control section 214. In other words, the maximum value N is defined such that the time resulting from the multiplication of the cycle of the watch-dog clear timer signal WDCK_HW by the maximum value N of the number of pulses can be equal to the time until the CPU 211 completes the initialization normally (the time estimated based on the design).

In FIG. 8, the CPU 211 completes the initialization normally before the count value K reaches the maximum value N in the counter in the watch-dog control section 214. Upon completion of the initialization in the CPU 211, the completion-of-initialization notification signal SEL to be outputted from the CPU 211 to the watch-dog control section 214 is switched from LOW to HIGH. Furthermore, upon completion of the initialization in the CPU 211, a watch-dog-timer clear signal WDCK, which is a pulse signal at predetermined intervals, is outputted from the CPU 211 to the watch-dog control section 214.

In the watch-dog control section 214 in response to the receipt of the completion-of-initialization notification signal SEL at HIGH, the watch-dog clear timer signal WD_CLR to be outputted to the watch dog timer IC 202 is switched from the watch-dog clear timer signal WDCK_HW received from the watch-dog clear signal generating section 213 to the watch-dog-timer clear signal WDCK received from the CPU 211. After that, under the state that the CPU 211 is normally operating, the watch dog timer IC 202 receives the watch-dog clear timer signal WD_CLR from the watch-dog control section 214 and continues monitoring the presence of the abnormality in the CPU 211.

Next, with reference to the timing chart in FIG. 9, an abnormality monitoring operation will be described in a case where an abnormality occurs during the startup of the CPU 211 and the initialization is not completed. Since the operation in the period from the powering-on of the electronic endoscopic apparatus to the start of the initialization of the CPU 211 is identical to the normal operation described with reference to FIG. 8, only an operation during the implementation of the initialization of the CPU 211 will be described herein.

During the implementation of the initialization of the CPU 211, the completion-of-initialization notification signal SEL at LOW is outputted from the CPU 211 to the watch-dog control section 214. In the watch-dog control section 214, the watch-dog clear timer signal WDCK_HW received from the watch-dog clear signal generating section 213 is outputted to the watch dog timer IC 202 as the watch-dog-timer clear signal WD_CLR, and the number of times of output of the watch-dog clear timer signal WDCK_HW as the watch-dog-timer clear signal WD_CLR (the number of outputted pulses) is counted as the count value K by the counter, not shown.

In FIG. 9, since an abnormality occurs during the implementation of the initialization and the CPU 211 does not complete the initialization, the completion-of-initialization notification signal SEL at LOW is outputted from the CPU 211 to the watch-dog control section 214 even if the count value K reaches the predefined maximum value N of the number of pulses. When the count value K reaches the maximum value N, the output of the watch-dog-timer clear signal WD_CLR from the watch-dog control section 214 to the watch dog timer IC 202 is stopped. In the watch dog timer IC 202, the fact that an abnormality has occurred in the CPU 211 is detected since the next pulse is not received even after the passage of the predefined timeout period from the receipt of the last pulse of the watch-dog-timer clear signal WD_CLR from the watch-dog control section 214. Thus, after the passage of the timeout period, the reset signal WD_RST_N is outputted from the watch dog timer IC 202 to the CPU 211.

In this way, in the electronic endoscopic apparatus according to the present embodiment during the implementation of the initialization by the CPU 211, the watch-dog clear timer signal WDCK_HW, which is a pulse signal at arbitrary intervals, generated by the watch-dog clear signal generating section 213 is outputted to the watch dog timer IC 202 as the watch-dog-timer clear signal WD_CLR. Thus, the repetitive restart of the CPU 211 during the initialization can be prevented even by using the watch dog timer IC 202 having a shorter timeout period than the startup time of the CPU 211.

Furthermore, the use of the watch dog timer IC 202 having a shorter timeout period allows quick reset and recovery of the CPU 211 in a case where the CPU 211 has an abnormality and runs away in the normal use mode.

Furthermore, whether the initialization of the CPU 211 has been completed within a designed initialization implementation time or not can be detected by counting, by the watch-dog control section 214, the number of times of output of the watch-dog clear timer signal WDCK_HW as the watch-dog-timer clear signal WD_CLR (the number of outputted pulses), which corresponds to the initialization implementation time of the CPU 211. In a case where the CPU 211 has an abnormality and runs away during the implementation of the initialization and falls into the state that prevents the completion of the initialization, the CPU 211 can be reset and recovered by stopping the output of the watch-dog-timer clear signal WD_CLR from the watch-dog control section 214 to the watch dog timer IC 202.

Furthermore, turning pins excluding a specific pin of the FPGA 201 to the high-impedance state during the implementation of the configuration of the FPGA 201 can prevent the reset operation during the implementation of the configuration of the FPGA 201 even in a case where the time for implementing the configuration by the FPGA 201 is longer than the timeout period of the watch dog timer IC 202.

[Third Embodiment]

Figure 10:
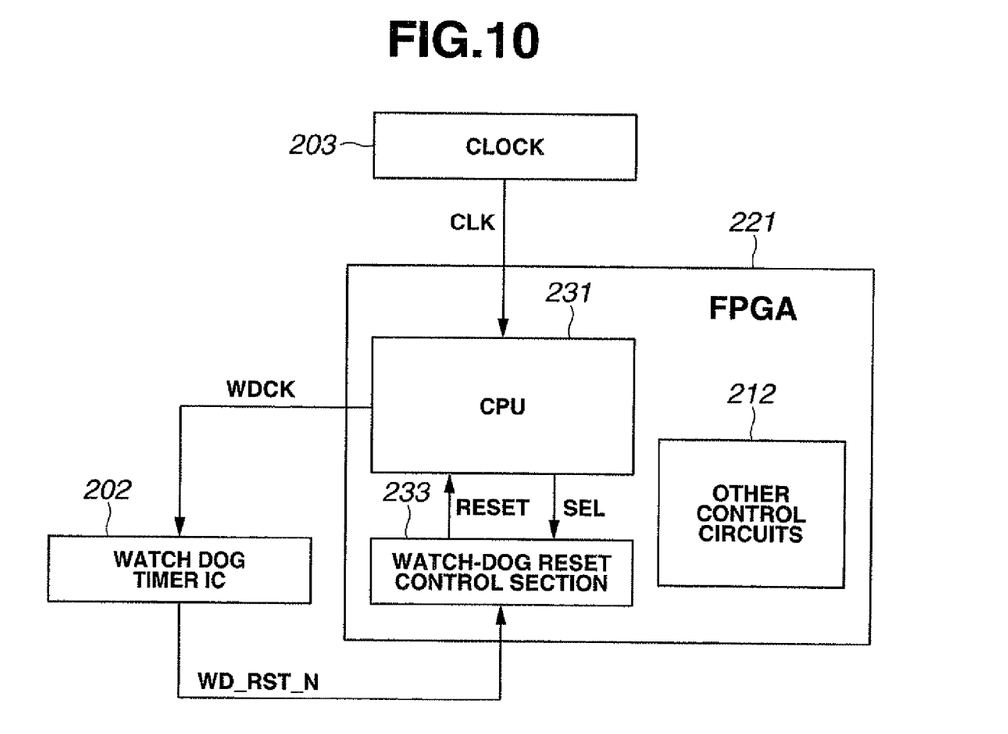
FIG. 10 is a block diagram illustrating a configuration of an abnormality monitoring section relating to a controller of an electronic endoscopic apparatus according to a third embodiment of the present invention.

Next, with reference to FIG. 10, a third embodiment of the present invention will be described. FIG. 10 is a block diagram illustrating a configuration of an abnormality monitoring section relating to a controller of an electronic endoscopic apparatus according to a third embodiment of the present invention. According to the second embodiment described above, the output of the reset signal WD_RST_N from the watch dog timer IC 202 is prevented by outputting the watch-dog clear timer signal WDCK_HW, which is a pulse signal at arbitrary intervals, generated by the watch-dog clear signal generating section 213 to the watch dog timer IC 202 during the implementation of the initialization of the CPU 211, and the reset operation in the CPU 211 during the implementation of the initialization is thus avoided. On the other hand, according to the present embodiment, the reset operation of a CPU 231 during the implementation of the initialization is avoided by voiding the reset signal WD_RST_N outputted from the watch dog timer IC 202 during the implementation of the initialization of the CPU 231.

Since the abnormality monitoring section relating to the controller of the electronic endoscopic apparatus is identical to that of the second embodiment except for the internal configuration of an FPGA 221, which is the controller to be monitored, only the internal configuration of the FPGA 221 will be described herein. The same reference numerals are given to the same components, and the description will be omitted herein. The same reference signs are given to the same signals among the signals outputted from the components, and the description will be omitted herein.

As shown in FIG. 10, the FPGA 221 includes a CPU 231, other control sections 212, and a watch-dog reset control section 233. The other control sections 212 control parts, such as a memory and a front panel, of the electronic endoscopic apparatus. The watch-dog reset control section 233 functions as a reset signal generating section that determines whether the CPU 231 is to be caused to perform the reset operation or not and outputs the reset signal RESET to the CPU 231. Notably, the completion-of-initialization notification signal SEL and the watch-dog-timer clear signal WDCK are outputted from the CPU 231 to the watch-dog reset control section 233 and the watch dog timer IC 202, respectively.

The watch-dog reset control section 233 outputs the reset signal RESET to the CPU 231 based on the reset signal WD_RST_N outputted from the watch dog timer IC 202 and the completion-of-initialization notification signal SEL outputted from the CPU 231. In other words, the reset signal RESET is outputted to the CPU 231 if the completion-of-initialization notification signal SILL at HIGH is received and if the reset signal WD_RST_N is further received. The reset signal RESET is also outputted to the CPU 231 if the reset signal WS_RST_N is received a specific number of times N' or more even in a case where the completion-of-initialization notification signal SEL at LOW is received. Here, the specific number of times N' is defined such that the time resulting from the multiplication of the cycle of the reset signal WD_RST_N by the specific number of times N' of pulses can be equal to the time until the CPU 231 normally completes the initialization (which is estimated from the design).

Under this configuration, since the watch-dog-timer clear signal WDCK is not outputted from the CPU 231 during the implementation of the initialization by the CPU 231, the reset signal WD_RST_N is outputted from the watch dog timer IC 202 but the reset operation can be avoided by the watch-dog reset control section 233. Notably, the watch-dog reset control section 233 has a startup monitoring section that monitors the state of the startup of the controller. Then, the watch-dog reset control section 233 monitors the time for implementing the initialization by the CPU 231 and outputs the reset signal WD_RST_N, which is outputted from the watch dog timer IC 202 from the watch-dog reset control section 233 to the CPU 31 as the reset signal RESET in a case where the CPU 211 has an abnormality and runs away during the implementation of the initialization and falls in the state that the initialization may not be completed. Thus, the CPU 231 can be reset to recover.

[Fourth Embodiment]

Figure 11:
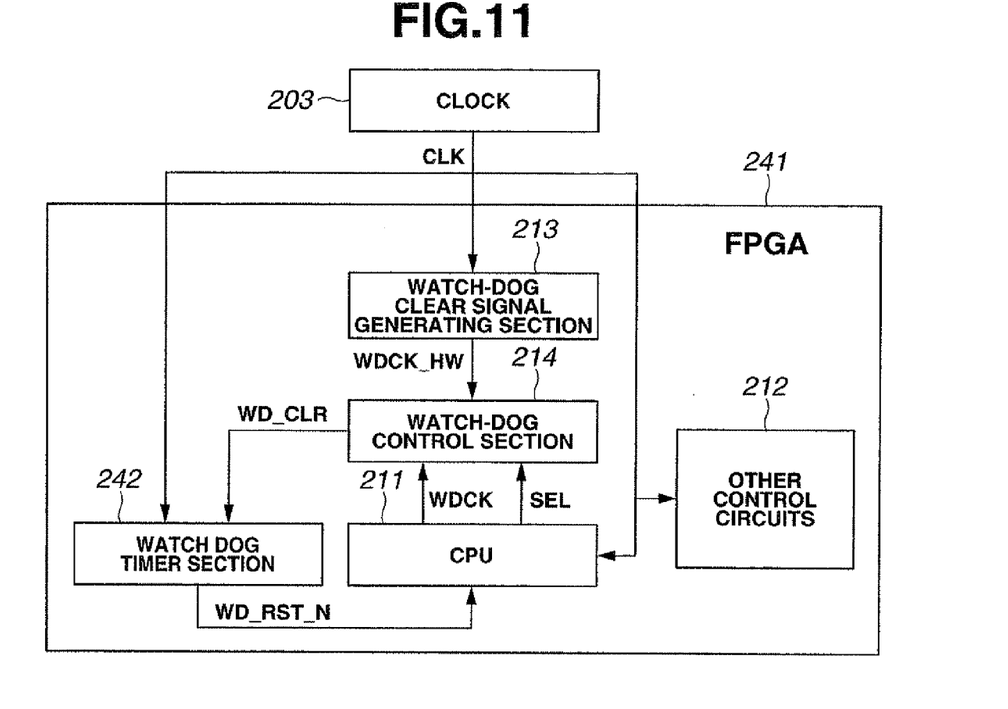
FIG. 11 is a block diagram illustrating a configuration of an abnormality monitoring section relating to a controller of an electronic endoscopic apparatus according to a fourth embodiment of the present invention.

Next, with reference to FIG. 1, a fourth embodiment of the present invention will be described. FIG. 11 is a block diagram illustrating a configuration of an abnormality monitoring section relating to a controller of an electronic endoscopic apparatus according to a fourth embodiment of the present invention. The present embodiment is different from the second embodiment in that a watch dog timer section 242 is deployed within an FPGA 241 while the watch dog timer IC 202 is deployed in the outside of the FPGA 201 according to the second embodiment. The watch dog timer section 242 outputs the reset signal WD_RST_N to the CPU 211 to implement a reset operation if the watch-dog-timer clear signal WD_CLR is not inputted from the watch-dog control section 214 within a predefined timeout period, like the watch dog timer IC 202. The other components and the signals to be outputted from the components are the same as those according to the second embodiment.

The deployment of the watch dog timer section 242 within the FPGA 241 allows arbitrary definition of the timeout period of the watch dog timer section 242, which increases the flexibility in design. Furthermore, since the watch dog timer section 242 does not operate until the configuration of the FPGA 241 completes, the reset operation can be securely avoided, without outputting the reset signal WD_RST_N during the configuration.

[Fifth Embodiment]

Figure 12:
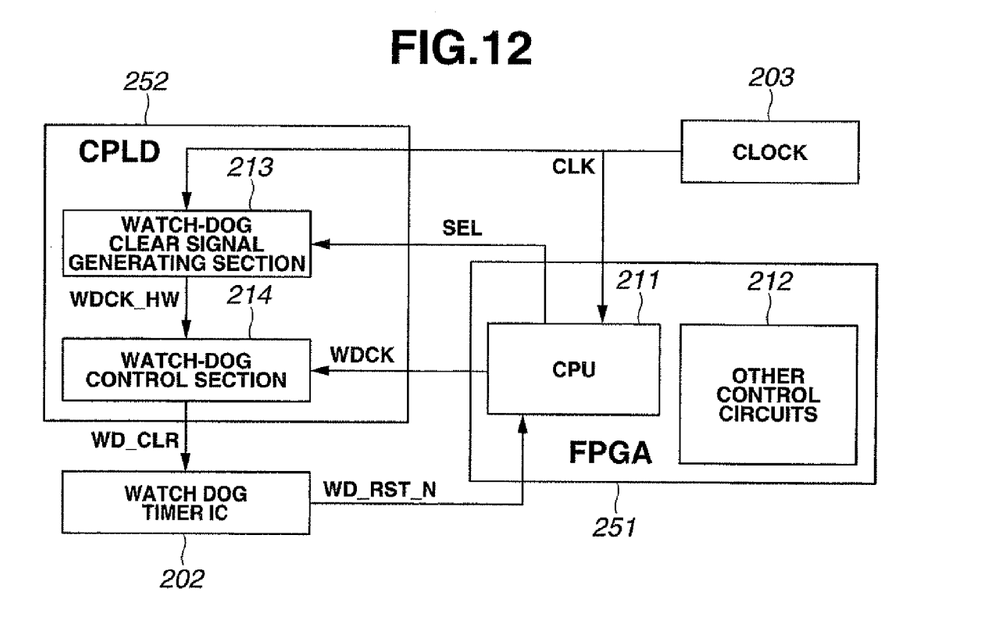
FIG. 12 is a block diagram illustrating a configuration of an abnormality monitoring section relating to a controller of an electronic endoscopic apparatus according to a fifth embodiment of the present invention.

Next, with reference to FIG. 12, a fifth embodiment of the present invention will be described. FIG. 12 is a block diagram illustrating a configuration of an abnormality monitoring section relating to a controller of an electronic endoscopic apparatus according to a fifth embodiment of the present invention. The present embodiment is different from the second embodiment in that the watch-dog clear signal generating section 213 and the watch-dog control section 214 are deployed in the outside of an FPGA 251 while they are deployed within the FPGA 201 according to the second embodiment.

According to the present embodiment, as shown in FIG. 12, a CPLD 252 may be provided in the outside of the FPGA 251, and the watch-dog clear signal generating section 213 and the watch-dog control section 214 may be deployed within the CPLD 252, for example. The CPLD 252 is configured to complete the configuration earlier than that of the FPGA 251. This can avoid an unnecessary reset operation while, in a case where the FPGA 251 completes the configuration earlier than that of the CPLD 252, a time lag may occur during the period from the completion of the configuration by the FPGA 251 to the output of the watch-dog-timer clear signal WD_CLR to the watch dog timer IC 202, which may possibly cause a reset operation. The other components and the signals outputted from the components are the same as those according to the second embodiment.

This configuration provides the same effects as those of the second embodiment and further increases the flexibility in design.

In a variation example of the fifth embodiment, a watch dog timer section may be deployed within the CPLD 252, instead of the watch dog timer IC 202. This configuration can avoid an unnecessary reset operation even in a case where the FPGA 251 completes the configuration earlier than that of the CPLD 252 since the watch dog timer section does not operate until the configuration of the CPLD 252 completes.

As described above, the electronic endoscopic apparatus according the second to fifth embodiments can implement an electronic endoscopic apparatus that has an abnormality monitoring section that detects an abnormality of the controller and causes to implement a reset operation and can prevent a CPU from repetitively restarting even by using a watch dog timer having a shorter timeout period than the startup time of the CPU.

The present application is based on Japanese Unexamined Patent Application No. 2005-195407 applied in Japan on Jul. 4, 2005 and Japanese Unexamined Patent Application No. 2005-181153 applied in Japan on Jun. 21, 2005 for claim of priority, the entire contents of which being incorporated in the specification and claims by reference.

The invention claimed is:

1. An electronic endoscopic apparatus having multiple operation modes to be executed exclusively, the apparatus comprising:
   a control section that controls the execution of the multiple operation modes, the control section including an FPGA in which a CPU is configurable, a non-volatile memory, and a download section;
   a switching request detecting section that detects a switching request for switching to the operation mode to be executed; and an in-machine abnormality detecting section that detects an internal abnormality of the electronic endoscopic apparatus;

wherein the download section includes a circuit that reads out configuration data of an operation mode to be executed from the non-volatile memory storing configuration data for the multiple operation modes and software and that downloads the read configuration data and the software to the FPGA;

wherein an internal configuration of the FPGA is changed to include the CPU in accordance with the operation mode according to the switching request detected by the switching request detecting section, the CPU being capable of executing the downloaded software related to the operation mode according to the switching request;

wherein the multiple operation modes include a safety mode; and wherein, when the electronic endoscopic apparatus has failed and the in-machine abnormality detecting section detects the internal abnormality while the control section is executing an operation mode other than the safety mode, the in-machine abnormality detecting section outputs an operation mode switching signal to the download section in order to switch the operation mode to the safety mode, and causes the download section to read out configuration data and software of the safety mode from the non-volatile memory and download the configuration data and software to the FPGA so that the internal configuration of the FPGA is changed to the safety mode which is an operation mode for a case where the electronic endoscopic apparatus has failed.

2. The electronic endoscopic apparatus according to claim 1, wherein the control section changes the internal configuration in accordance with the operation mode according to the switching request detected by the switching request detecting section during an initializing operation of the control section.

3. The endoscopic apparatus according to claim 1, wherein the download section comprises a CPLD.

4. An electronic endoscopic apparatus having multiple operation modes to be executed exclusively, the apparatus comprising:

a control section that controls the execution of the multiple operation modes, the control section including an FPGA in which a CPU is configurable, a non-volatile memory, a CPLD and a clock generator that generates a clock signal and outputs the clock signal to the FPGA and the CPLD;

a switching request detecting section that detects a switching request for switching to the operation mode to be executed; and an in-machine abnormality detecting section that detects an internal abnormality of the electronic endoscopic apparatus;

wherein the CPLD includes a circuit that reads out configuration data of an operation mode to be executed from the non-volatile memory storing configuration data for the multiple operation modes and software and that downloads the read configuration data and the software to the FPGA;

wherein an internal configuration of the FPGA is changed to include the CPU in accordance with the operation mode according to the switching request detected by the switching request detecting section, the CPU being capable of executing the downloaded software that is related to the operation mode according to the switching request;

wherein the multiple operation modes include a safety mode; and wherein, when the electronic endoscopic apparatus has failed and the in-machine abnormality detecting section detects the internal abnormality while the control section is executing an operation mode other than the safety mode, the in-machine abnormality detecting section outputs an operation mode switching signal to the CPLD in order to switch the operation mode to the safety mode, and causes the CPLD to read out configuration data and software of the safety mode from the non-volatile memory and download the configuration data and software to the FPGA so that the internal configuration of the FPGA is changed to the safety mode which is an operation mode for a case where the electronic endoscopic apparatus has failed.

5. The electronic endoscopic apparatus according to claim 4, wherein the control section changes the internal configuration in accordance with the operation mode according to the switching request detected by the switching request detecting section during an initializing operation of the control section.

* * * * *